United States Patent [19]

Comstock

[11] Plant 4,995

[45] Mar. 15, 1983

[54] BOUGAINVILLEA SELECTION

[75] Inventor: Clifton C. Comstock, Glendora, Calif.

[73] Assignee: Monrovia Nursery Company, Azusa, Calif.

[21] Appl. No.: 275,867

[22] Filed: Jun. 22, 1981

[51] Int. Cl.[3] ..... A01H 5/00

[52] U.S. Cl. ..... Plt./54

[58] Field of Search ..... Plt./54

*Primary Examiner*—Robert E. Bagwill

[57] ABSTRACT

A new and distinct variety of Bougainvillea vine (popularly known by the same name). A chance seedling selection of a plant with a combination of superior qualities of (1) large flower bracts; (2) vibrant purple colored bracts; (3) deeper and more colorful purple pubescent new growth.

2 Drawing Figures

DISCOVERY

This invention relates to a new and distinct variety of Bougainvillea, a member of the Nyctaginaceae family. This new variety was selected from a seedling bed of Bougainvillea at Monrovia Nursery Company, 18331 E. Foothill Blvd., Azusa, Calif., on May 1, 1976.

The plant to date is known to exist only within the boundaries of Monrovia Nursery and has not been offered for sale or described in any publication.

REPRODUCTION

This new variety has been strictly asexually reproduced at Monrovia Nursery. This variety is a seedling selection with distinct qualities that separate it from other seedlings. Therefore, seed propagation is prohibited and propagation is restricted to vegetative cuttings.

CHARACTERISTICS

This new selection differs from other known selections by a combination of characteristics which make this a superior plant. The first attribute is a combination of our selections's large and vibrant purple flower bracts (see description and photo enclosed). These large and vibrant purple flower bracts make this selection extremely desirable for ornamental uses.

The second attribute is our selection's deeper and more colorful purple pubescent new growth (see description and photo). Many of the present day selections of Bougainvillea have glabrous new growth. Of those which are pubescent none show the new growth as such a deep and intense purple velvet in texture and appearance. The combination of these aesthetically important qualities makes our selection a superior plant.

DESCRIPTION

Below is a detailed description of the new variety, all color terminology is from The British Horticultural Colour Charts.

Habit of plant is an evergreen vine.

FLOWER

Calyx: Tubular ¾ inch long, finely pubescent with five longitudinal ribs and five shallow lobes, Pansy Purple 928.

Calyx petaloids: Five in number, 1/16 to ⅛ inch in length Lemon Yellow 4/3, attached to calyx lobes on three sides.

Arrangement: Flowers in clusters of three, each attached by the pedicel to one persistent showy bract.

BRACT

Color: Mature bracts a mixture of Garnet Lake 828/2 and Doge Purple 732.

Size: 1½ to 1¾ inch in length, by 1¼ to 1½ inch width.

Shape: Oblong to orbicular with cordate base and mucronate tip.

LEAF

Arrangement: Alternate

Development: New leaves are completely Maroon 1030 and velutinous as are the young branches and petioles. As leaf ages to the juvenile stage the purple color persists on margins, petioles, midribs and young branchlets eventually changing in the mature stage to green with a sparser pubescense on older portions of branchlets and petioles.

Juvenile:

*Size.*—1½ to 2¼ inch in length, 1½ to 1¾ inch width.

*Color.*—Varying in blendings of Parsley Green 00962/1 and Garnet Lake 828.

*Shape.*—Ovate to elliptic, with cuneate to truncate base and acuminate tip; margins entire and undulate.

*Pubescense.*—Finely pubescent on all leaf surfaces.

LEAF

Mature:

*Size.*—1¼ to 5 inch in length; 1¼ to 3¾ inch in width.

*Color.*—Upper side — Parsley Green 0092/1. Lower side — Spinach Green 0960/3.

*Shape.*—Deltoid to ovate with obtuse, cuneate base and narrow acuminate tip; margins entire.

*Pubescense.*—Finely puberulent along midrib and upper and lower leaf surface.

FRUIT

Not significant.

I claim:

1. A new and distinct selection of Bougainvillea as substantially shown and described, a selection characterized by a superior combination of unusually large and vibrant purple colored flower bracts and a deeper and more colorful purple pubescent new growth.

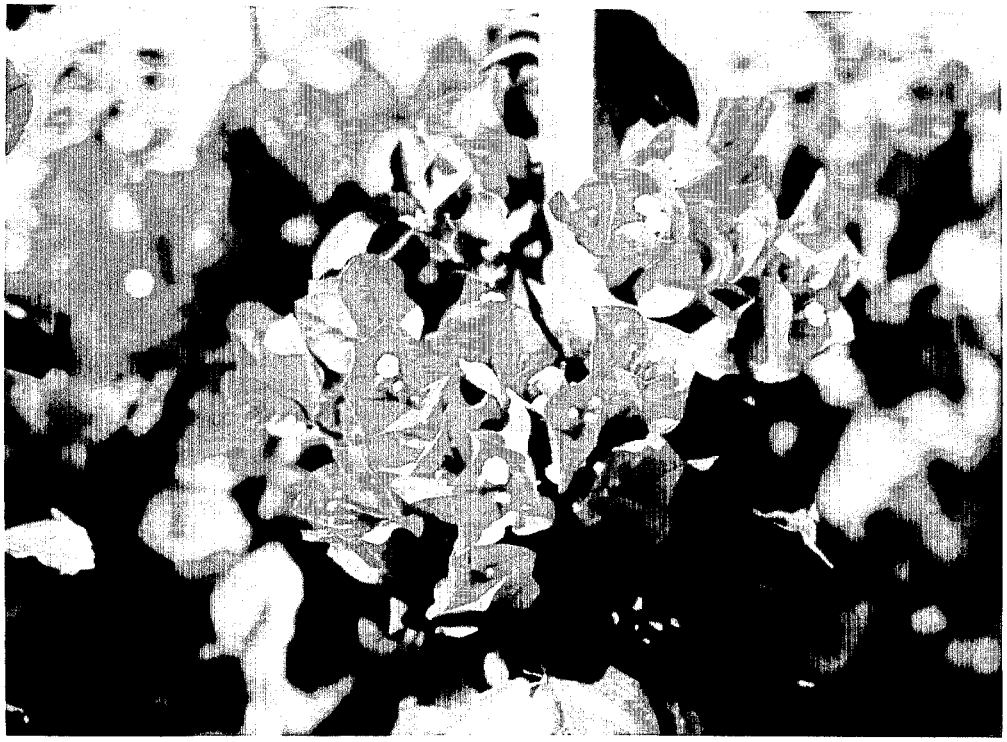
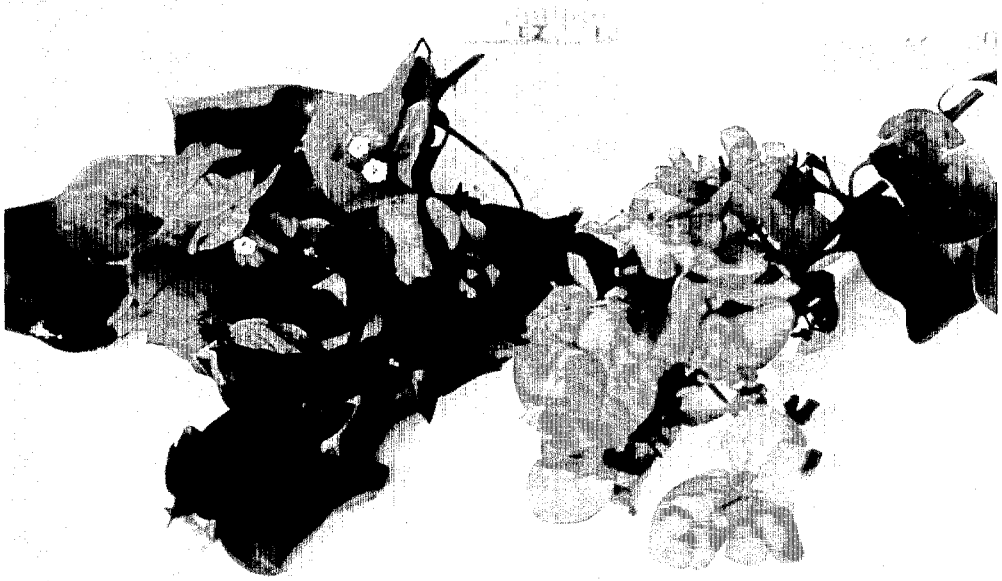

* * * * *